United States Patent
Yoshida et al.

(10) Patent No.: US 8,649,480 B2
(45) Date of Patent: Feb. 11, 2014

(54) X-RAY CT APPARATUS AND TOMOGRAPHY METHOD

(75) Inventors: Ryo Yoshida, Tokyo (JP); Yoshiaki Sugaya, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 345 days.

(21) Appl. No.: 13/254,634

(22) PCT Filed: Mar. 4, 2010

(86) PCT No.: PCT/JP2010/053508
§ 371 (c)(1),
(2), (4) Date: Sep. 2, 2011

(87) PCT Pub. No.: WO2010/101208
PCT Pub. Date: Sep. 10, 2010

(65) Prior Publication Data
US 2012/0002782 A1 Jan. 5, 2012

(30) Foreign Application Priority Data
Mar. 6, 2009 (JP) .................................. 2009-052770

(51) Int. Cl.
*A61B 6/00* (2006.01)
(52) U.S. Cl.
USPC ............................................. 378/16; 378/20
(58) Field of Classification Search
USPC ........................................ 378/4–20, 156–159
See application file for complete search history.

(56) References Cited

U.S. PATENT DOCUMENTS
2004/0202283 A1 10/2004 Okumura et al.

FOREIGN PATENT DOCUMENTS
| JP | 2004-180715 | 7/2004 |
| JP | 2005-13489 | 1/2005 |
| JP | 2007-267783 | 10/2007 |

OTHER PUBLICATIONS
International Search Report in PCT/JP2010/053508, Apr. 13, 2010.

*Primary Examiner* — Courtney Thomas
(74) *Attorney, Agent, or Firm* — Cooper & Dunham LLP

(57) ABSTRACT

When the diagnostic center position and a reconstruction FOV are designated using a tomographic image, a system control device controls a top plate of a table to move from side to side and up and down so that the designated diagnostic center position reaches the center position of scanning. A scanner is provided with a plurality of compensation filters configured to adjust X-ray irradiation distribution, and the system control device selects a proper compensation filter according to the designated reconstruction FOV from among the plurality of compensation filters, switching to the selected compensation filter. The compensation filters include at least a compensation filter (size L) of wide-width X-ray irradiation distribution and a compensation filter (size S) of narrow-width X-ray irradiation distribution in a scanner-turning direction. When the designated reconstruction FOV is a predetermined threshold or less, the compensation filter is switched to the S-sized compensation filter.

6 Claims, 10 Drawing Sheets

X-RAY CT APPARATUS AND TOMOGRAPHY METHOD

FIELD OF THE INVENTION

The present invention relates to movement control of table positions and switching control of compensation filters in an X-ray CT apparatus.

DESCRIPTION OF RELATED ART

An X-ray CT apparatus irradiates an X-ray of a fan beam or cone beam (conical shape or pyramid shape beam) from an X-ray source which is provided in a scanner to an object to be examined, acquires the X-ray data transmitted through an object (transmission X-ray data) by an X-ray detector, and reconstructs a tomographic image etc. of the object by an image reconstruction device based on the acquired transmission X-ray data.

In such an X-ray CT apparatus, an operator first places the object on a table, and adjusts the position of the object so that the center of the object on the table in the side-to-side direction and the center of the object in the body-thickness direction matches the revolution center of the scanner using a laser projector and the like that points out the center position for scanning. Then the operator executes scanogram to project the object on a scanogram image, and sets the scanning range in the body-axis direction, the center of the reconstructed image or reconstruction FOV (Field Of View) while referring to the scanogram image in the PA direction (the direction viewed from the front of a body) and/or in the LAT direction (the direction viewed from the side of a body) constructed by an image reconstruction device. The position information or reconstruction FOV being set as described above is transmitted to the table and the scanner, and the helical scanning or axial scanning and the like is started after the table position is properly adjusted.

An X-ray CT apparatus is equipped with a compensation filter for adjusting irradiation distribution of X-rays. The compensation filter is to be provided between an X-ray tube and the object, and thickness of the filter is configured different depending on the position of the scanner's scanner-turning direction so that the X-ray dose becomes the greatest in the center of the scan and smaller as the position gets closer to the periphery.

Patent Document 1 in relation to the positioning of a table discloses the X-ray CT apparatus which translates the center position of scan (hereinafter referred to a diagnostic center position) by varying the table position in the side-to-side direction (perpendicular to the body axis and parallel to the table plate) and the up-and-down direction (perpendicular to the body axis and perpendicular to the table plate) during a helical scan. In this X-ray CT apparatus, the place to be set as the diagnostic center position is designated from two directions on a scanogram image in the PA direction and the LAT direction upon planning the scan range, etc.

Also in Patent Document 2, a gantry device, etc. are disclosed for changing the filter in accordance with a scanning area. In addition, the filter disclosed in Patent Document 2 is for adjusting the X-ray intensity which is different from the filter for adjusting X-ray irradiation distribution.

In Patent Document 3, the X-ray CT apparatus is disclosed which designates the center of a diagnostic target region from a scanogram image, moves the top plate in the direction orthogonal to the body axis so as to place the center of the diagnostic target region at the center of scanning, selects the wedge (compensation filter) being coordinated with the shape of the target region and adjust irradiation range of the X-ray.

PRIOR ART DOCUMENTS

Patent Document 1: JP-A-2008-167804
Patent Document 2: JP-A-2002-102217
Patent Document 3: JP-A-2007-267783

However, as disclosed in Patent Document 1 and Patent Document 3, when a diagnostic center position is to be designated using a scanogram image, it has been difficult to accurately designate the center of a target organ due to overlap of different organs or overlap of a bone and an organ.

Also in Patent Document 2, a scan region in an object to be examined is designated by selecting a scan region such as a "head region", "chest region" or "abdominal region" from a menu screen. However, while high spatial resolution is required when observing a detailed area such as a coronary artery of a heart region and the X-ray that satisfy such condition is necessary, if the heart region is at an offset position from the center of scanning, such condition causes the lowering of spatial resolution and irradiation of large dose of X-ray even to the other organs besides the heart region.

Considering the above-described problems, the objective of the present invention is to provide the X-ray CT apparatus capable of executing accurate designation of a region of interest and reducing exposure dose to the other regions besides the designated region while improving image quality of the region of interest.

BRIEF SUMMARY OF THE INVENTION

In order to achieve the above-described objective, the X-ray CT apparatus related to the present invention comprises:
a scanner in which an X-ray source for irradiating an X-ray to an object to be examined and an X-ray detector for detecting the X-ray which transmitted through the object are placed opposite from each other, which revolves around the object; and
a table having a top plate movable in the body-axis direction, the side-to-side direction and up-and-down direction while being perpendicular to the body-axis direction,
configured to reconstruct a tomographic image of the object based on the transmitted X-ray data detected by the X-ray detector and display the reconstructed image on display means,
wherein the scanner is provided with a compensation filter configured to adjust irradiation distribution of the X-ray irradiated from the X-ray source,
characterized in further comprising:
designation means configured to receive the designation of the diagnostic center position and reconstruction FOV of the object using the tomographic image;
top plate moving means configured to move a top plate of the table in the body-axis direction, the side-to-side direction or the up-and-down direction so that the diagnostic center position designated by the designation means reaches a scanning center position; and
scanning means configured to execute a tomography using contrast agent or with desired image quality in the condition that a top plate is moved by the top plate moving means.

Also, the present invention is a tomography method by an X-ray CT apparatus comprising:
a scanner in which an X-ray source for irradiating an X-ray to an object to be examined and an X-ray detector for detecting the X-ray which transmitted through the object are placed opposite from each other, which revolves around the object; and a table having a top plate movable in the body-axis direction, the side-to-side direction or up-and-down direction while being perpendicular to the body-axis direction, wherein the scanner is provided with a compensation filter configured to adjust irradiation distribution of the X-ray irradiated from the X-ray source, for reconstructing a tomographic image of the object based on the transmitted X-ray data detected by the X-ray detector and displaying the reconstructed image on display means, characterized in further comprising the steps of:

receiving the designation of a diagnostic center position and a reconstruction FOV of the object using the tomographic image;

moving the top plate of the table in the body-axis direction, the side-to-side direction or the up-and-down direction so that the diagnostic center position reaches a scanning center position; and executing a tomography using contrast agent or with desired image quality in the condition that a top plate is moved.

EFFECT OF THE INVENTION

In accordance with the X-ray CT apparatus of the present invention, it is possible to execute accurate designation of a region of interest and reduce exposure dose to the other regions besides the designated region while improving image quality of the region of interest.

DETAILED DESCRIPTION OF THE INVENTION

An embodiment of the present invention will be described in detail referring to the attached diagrams.

First Embodiment

First, configuration of the X-ray CT apparatus 1 in the present embodiment will be described referring to FIG. 1~FIG. 5.

Figure 1:
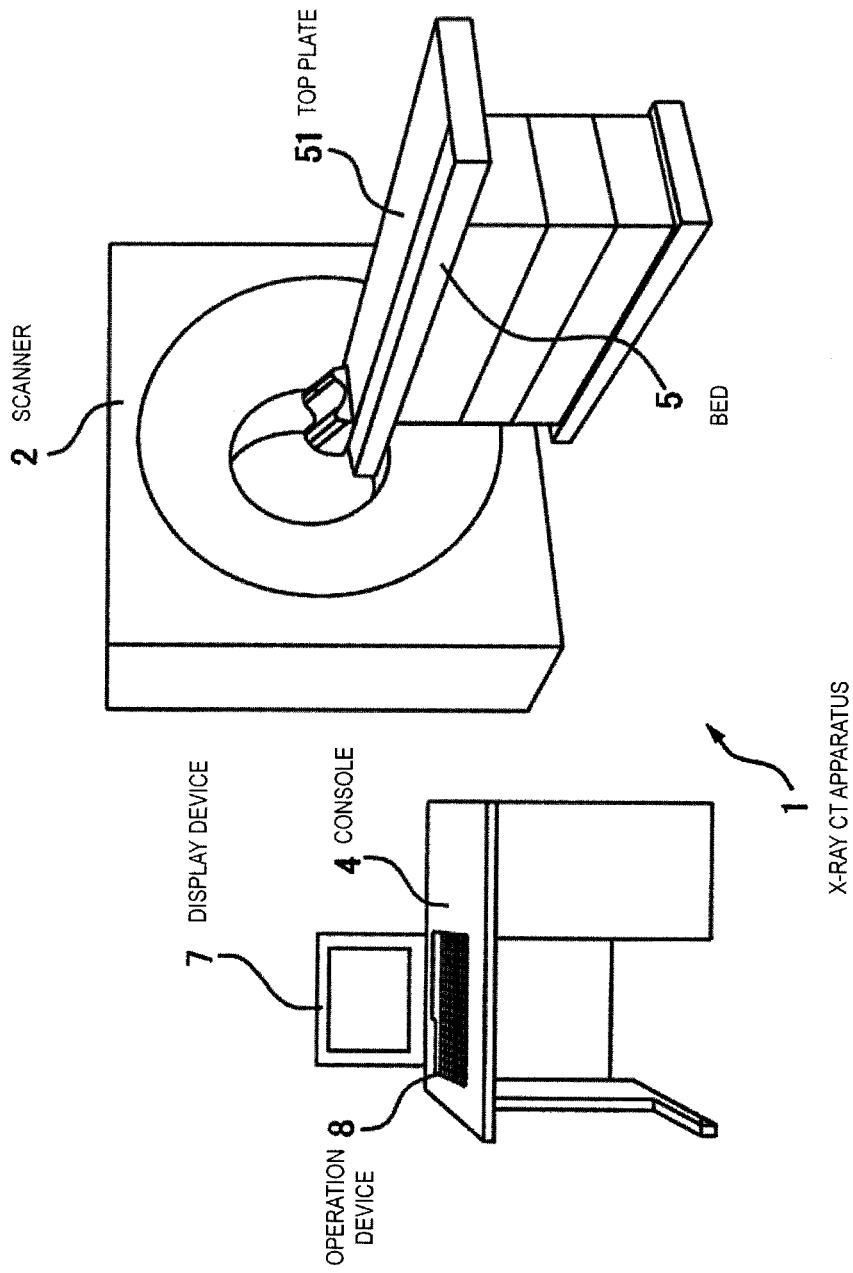
FIG. 1 is an external view showing the general configuration of an X-ray CT apparatus 1.

As shown in FIG. 1, the X-ray CT apparatus 1 is formed by a scanner 2, a console 4, a table 5, a display device 7 and an operation device 8. The X-ray CT apparatus 1 acquires the X-ray data transmitted through an object 6 (hereinafter referred to as transmitted X-ray data) by inserting the object 6 who is fixed on the table 5 into an apertural area of the scanner 2 and scanning the object.

The scanner 2 is formed by an X-ray tube 201, an X-ray control device 202, a collimator case 203, a compensation filter switch control device 204, an X-ray detector 205, a data collection device 206, a rotor plate 207, a rotor plate driving device 208, a revolution control device 209 and a power transfer system 210.

The X-ray tube 201 is an X-ray source, and executes continuous or intermissive X-ray irradiation to the object 6 under control of the X-ray control device 202. The X-ray control device 202 controls the X-ray tube voltage and X-ray tube current to be applied or supplied to the X-ray tube 201 according to the X-ray tube voltage or X-ray tube current determined by a system control device 401 of the console 4.

The collimator case 203 stores devices such as a collimator, a plurality of compensation filters and a switch mechanism 303 for the compensation filters. The collimator is for irradiating the X-ray emitted from the X-ray tube 201 to the object 6 as, for example a fan-beamed X-ray.

Figure 2:
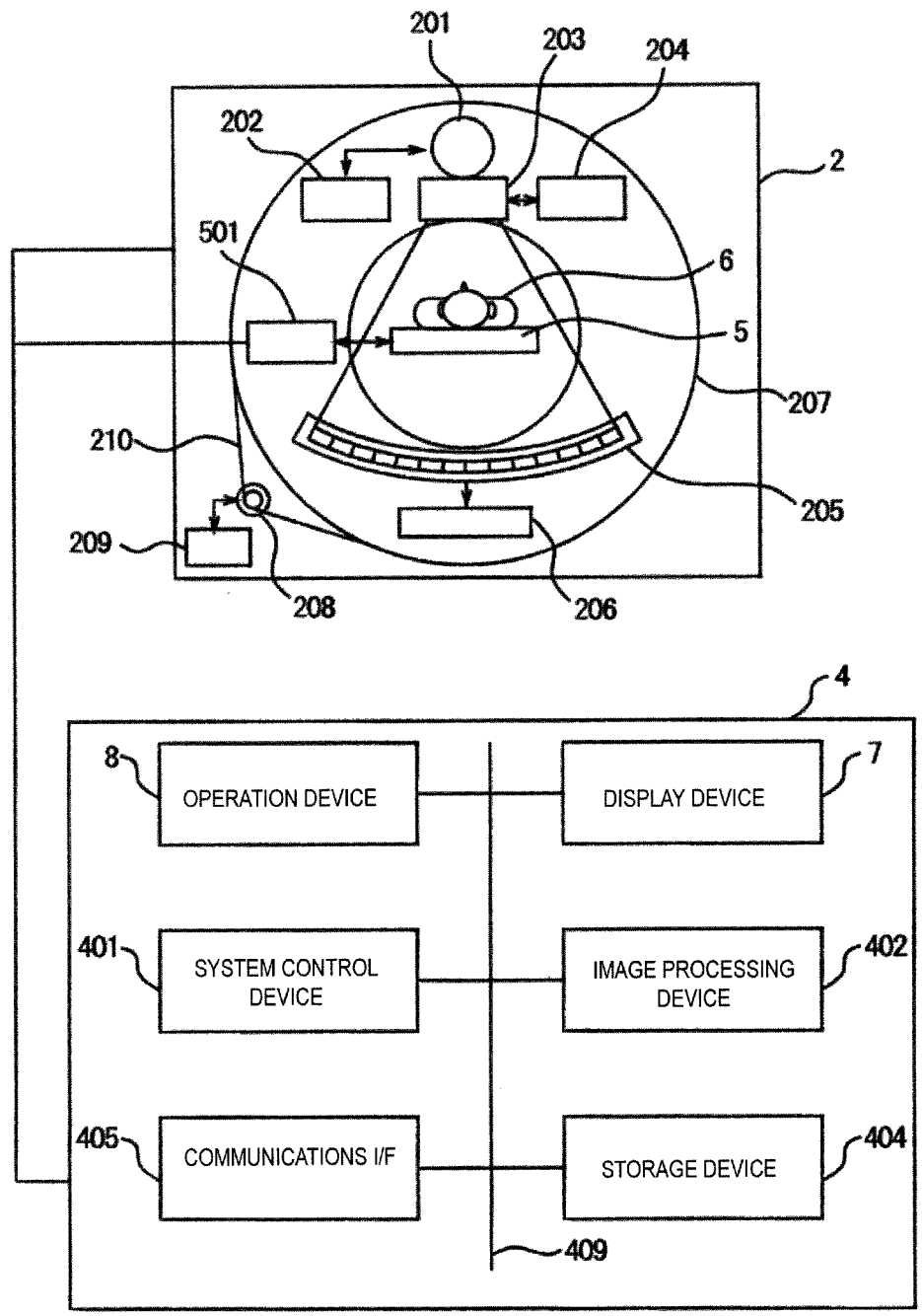
FIG. 2 is a hardware block diagram of the X-ray CT apparatus 1.

The compensation filter is for adjusting X-ray irradiation distribution, and a plurality of filters for different X-ray irradiation distributions are mounted. In the present embodiment, two compensation filters 301 and 302 are mounted which can be freely switched by the switch mechanism 303 as exemplified in FIG. 3. The switch mechanism 303 is under control of the compensation filter switch control device 204 (FIG. 2).

Figure 3:
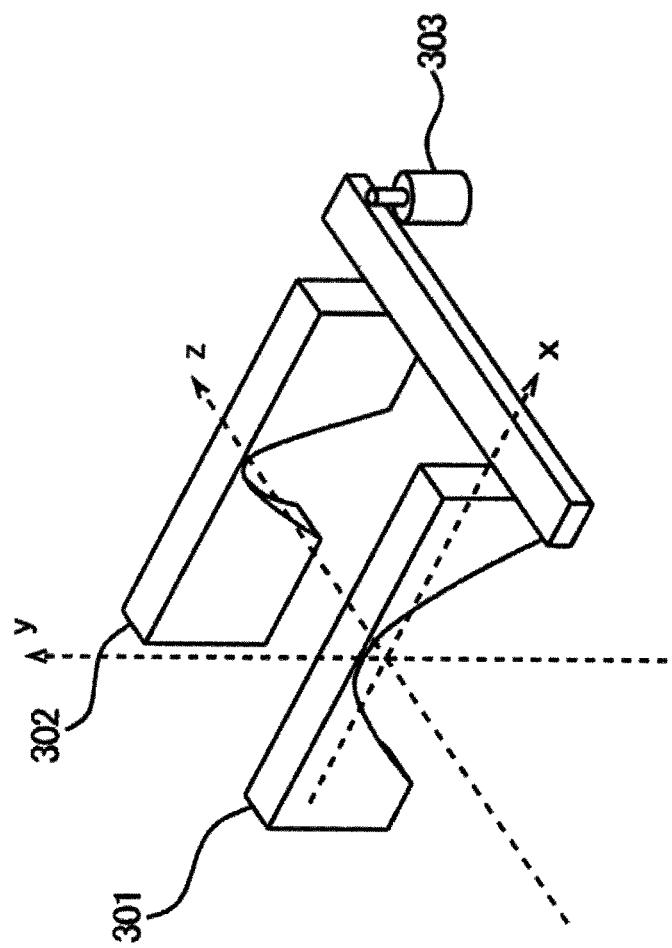
FIG. 3 is for explaining a compensation filter and a switching mechanism thereof.
Figure 4:
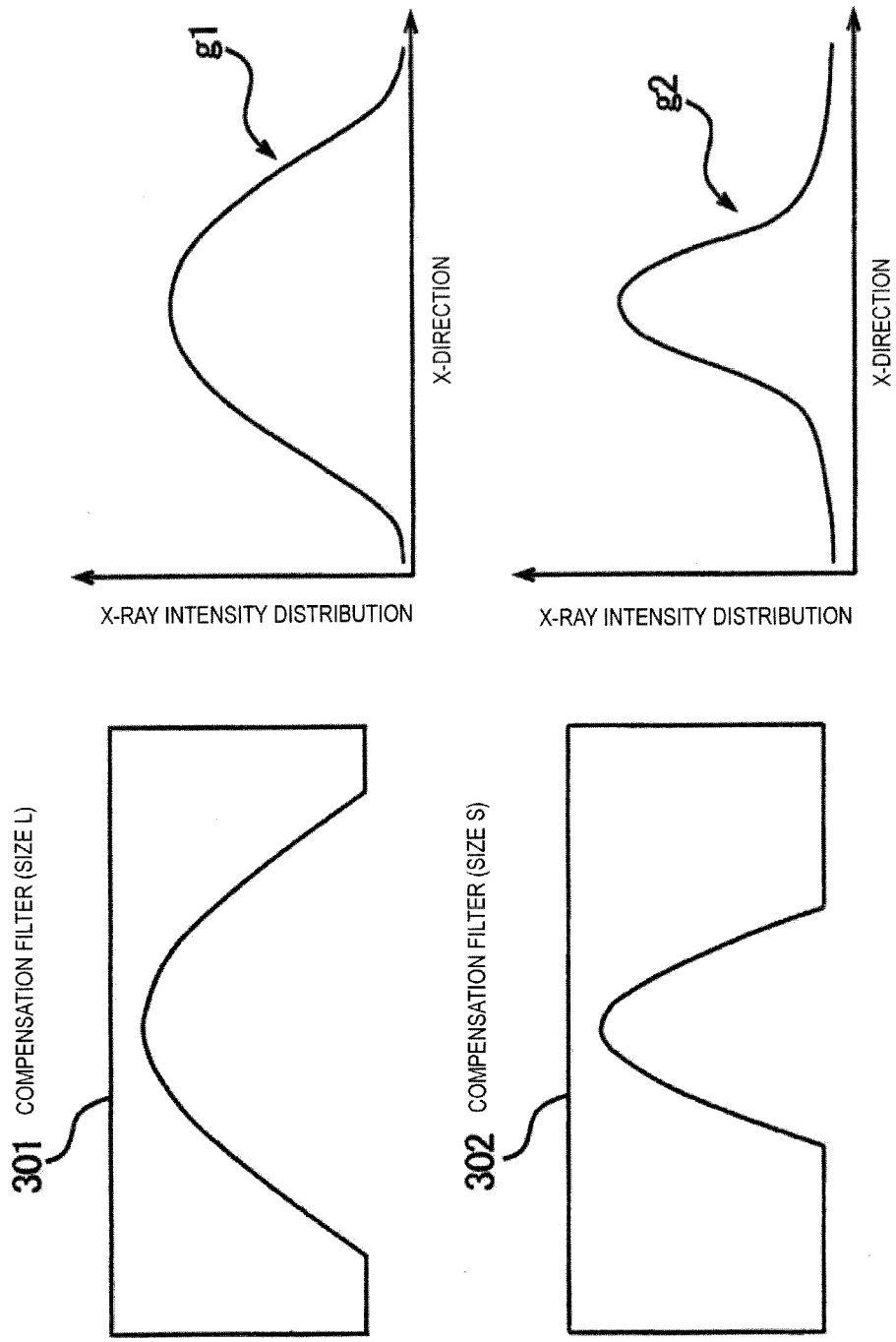
FIG. 4 shows compensation filters and graphs of X-ray intensity distribution thereof.

As shown in FIG. 3 and FIG. 4, compensation filters 301 and 302 adjust the X-ray dose irradiated from the X-ray tube 201 so that the X-ray intensity can be varied in accordance with the position of a scanner in the scanner-turning direction (x-direction in FIG. 3). Each of compensation filters 301 and 302 has a curved plane that causes the X-ray dose (X-ray intensity) to be the maximum in the center and to be reduced as the position gets away from the center symmetrically in the side-to-side direction (x-direction in FIG. 3). Also, the curvature of the curved plane in the compensation filter 301 is smaller than the curvature of the curved plane in the compensation filter 302. In other words, compensation filter 302 distributes an X-ray to a narrower range compared to the range to be distributed by the compensation filter 301.

Hereinafter the compensation filter 301 having a larger X-ray irradiation width is referred to an L-sized compensation filter, and the compensation filter 302 having a smaller X-ray irradiation width is referred to as a S-sized compensation filter.

A graph g1 in FIG. 4 shows the X-ray intensity distribution of the compensation filter 301, and a graph g2 shows the X-ray intensity distribution of the compensation filter 302. When these graphs g1 and g2 are compared, the compensation filter 302 irradiates an X-ray to a narrower range than the compensation filter 301. The L-sized compensation filter 301 is suitable for the scanning target having a large width such as an abdominal region, and the compensation filter 302 is suitable for the scanning target having a small radius such as a head region, a heart region to be described later, or a child.

The X-ray irradiated from the X-ray source 201 and transmitted through the object 6 via a compensation filter and a collimator is transmitted to the X-ray detector 205.

The X-ray detector 205 is formed by X-ray detection elements constituted by the combination of, for example scintilator and photo diode wherein about 1000 elements are arrayed in the scanner scanner-turning direction and 1~320 elements are arrayed in the row-direction (body-axis direction), and is disposed facing the X-ray tube 201 having the object 6 therebetween. The X-ray detector 205 detects the X-ray emitted from the X-ray tube 201 and transmitted through the object 6, and outputs the detected X-ray data to the data collection device 206.

The data collection device 206 is connected to the X-ray detector 205, and collects the transmitted X-ray data detected by each of X-ray detection elements of the X-ray detector 205. The collected X-ray data are outputted to an image processing device 402 of the console 4.

In the rotor plate 207 of the scanner 2, the X-ray tube 201, the collimator case 203, the X-ray detector 205 and the data collection device 206 are mounted. The rotor plate 207 is rotated by the drive force transmitted from the rotor plate driving device 208 controlled by the revolution control device 209 via the power transfer system 210.

Figure 5:
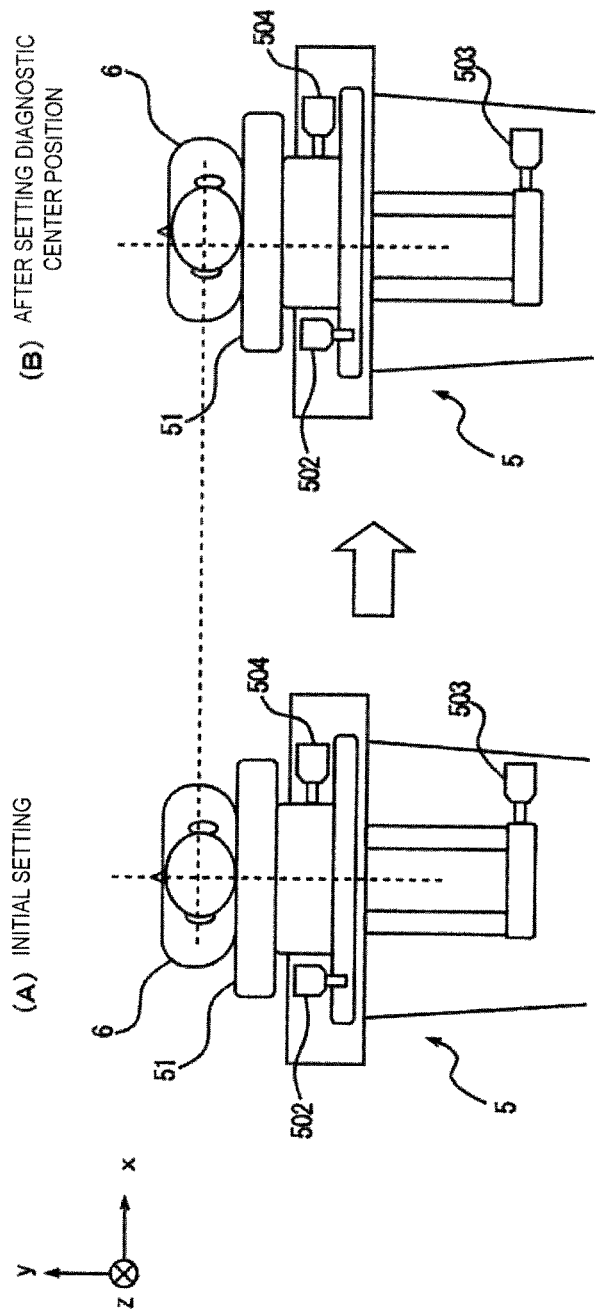
FIG. 5(A) is for explaining the initial setting position of a table, and (B) is for explaining the moved table position after designation of a diagnostic center position.

The table 5 is configured by a top plate 51 on which the object 6 is placed, a z-direction moving mechanism 504 for moving top the plate 51 in the body-axis direction (z-direction), an x-direction moving mechanism 502 for moving the top plate in the side-to-side direction (x-direction), a y-direction moving mechanism 503 for moving the top plate in the up-and-down direction (y-direction) and a table control device 501 (refer to FIG. 2) as shown in FIG. 5.

The table control device 501 adjusts the height of table 5 to a proper height by controlling the y-direction moving mechanism 503. Also, the table control device 501 controls the x-direction moving mechanism 502 or the z-direction moving mechanism 504 to move the top plate 51 backward and forward in the body-axis direction or in the direction perpendicular to the body axis and parallel to the top plate 51 (side-to-side direction). In this manner, the object 6 is carried in and out of an X-ray irradiation space of the scanner 2, and the diagnostic center position designated by an operator is positioned to reach the scanning center position.

The scanning center position means the center position of revolution in a scanner. In the following description, the body-axis direction is set as z-direction, the direction perpendicular to the body axis and parallel to the top plate 51 (side-to-side direction) is set as x-direction, and the direction perpendicular to the body axis and perpendicular to the top plate 51 (up-and-down direction) is set as y-direction in the coordinates representing the position of the top plate 51 of the table 5. Also, the side-to-side direction is set as X-direction and the up-and-down direction is set as Y-direction in the coordinates on a display screen of the display device 7.

Also in the following description, the position of the top plate 51 of the table 5 in the initial setting is referred to as the "scanning start point", and the coordinates thereof are set as $(x_0, y_0, z_0)$. The "diagnostic start position" is the center position of an image to be displayed on a display screen (a scanogram image or a tomographic image), and the coordinates on the display screen are set as $0$ $(X_0, Y_0)$ (refer to FIG. 7(C)). The "diagnostic center point" is the designated position on a display screen which is designated to reach the scanning center position at the time of actual scanning (plain scanning or contrast radiography), and the coordinates thereof are set as $01$ $(X_1, Y_1)$. The coordinates in the real space corresponding to diagnostic center position $01$ $(X_1, Y_1)$ are set as $(x_1, y_1, z_1)$.

As shown in FIG. 2, the console 4 is formed by the display device 7, the operation device 8, the system control device 401, the image processing device 402, a storage device 404 and a communications I/F 405, and these components are connected to each other via a bus 409. Also, the console 4 is connected to the scanner 2 and the table 5 via the communications I/F 405.

The display 7 is configured by display devices such as a liquid crystal panel and a CRT monitor and a logical circuit which is linked up with the display device for executing display processing, and is connected to the system control device 401. The display device 7 is for displaying a reconstructed image or scanogram image outputted from the image processing device 402 or various sorts of information handled by the system control device 401.

The operation device 8 is formed by a pointing device such as a keyboard or mouse, an operation device such as a numeric keypad and various switch buttons, and outputs various commands or information inputted by an operator to the system control device 401. The operator interactively operates the X-ray CT apparatus 1 using the display device 7 and the operation device 8. For example, the operation device 8 receives designation operation, etc. for moving the table position to a desired diagnostic center position based on the tomographic image (axial image) obtained by the image processing device 402.

The system control device 401 is configured by devices such as a CPU (Central Processing Unit), a ROM (Read Only Memory) and a RAM (Random Access Memory). The system control device 401 controls the X-ray control device 202, the compensation filter switch control device 204, the data collection device 206, the X-ray detector 205 and the revolution control device 209 in the scanner 2, and the table control device 501 in the table 5.

Also, system control device 401 executes the scanning process to be described later (refer to FIG. 6). In the scanning process, the system control device 401 receives designation of the diagnostic center position and reconstruction FOV. When an arbitrary diagnostic center position $01$ $(X_1, Y_1)$ is designated by the operation via the operation device 8 using a pointing device such as a mouse, the system control device 401 calculates moving distance of the top plate 51 so that the designated diagnostic center position $01$ $(X_1, Y_1)$ reaches the scanning center position, and controls the table control device 501 for moving the top plate 51 of the table 5 in the x-direction, y-direction or z-direction. Also, the system control device 401 selects suitable compensation filters 301 or 302 according to the designated reconstruction FOV and switches to the suitable one. The system control device 401, when the designated reconstruction FOV has the same or smaller value compared to a predetermined threshold value, switches the filter to the compensation filter which distributes an X-ray to a narrower width (size S).

Also, the X-ray CT apparatus 1 of the present embodiment, after obtaining scanogram image, executes plain scanning without using contrast agent, displays the tomographic image of the object (axial image) obtained by the plain scanning on the display device 7, and receives designation of the diagnostic center position and the reconstruction FOV by the command operation corresponding to the displayed tomographic image.

The image processing device 402 comprises a correction processing unit and an image reconstruction unit. The correction processing unit, upon acquiring the transmitted X-ray data collected by the data collection device 206, executes correction processing such as offset voltage correction and sensitivity correction of the errors included in the transmitted X-ray data or the X-ray detector, and outputs the compensated data to the image construction unit. The image reconstruction unit creates a scanogram image in the LAT direction or PA direction upon scanogram imaging using the compensated X-ray data. Also, at the time of actual scanning (plain scanning, contrast radiography or low dose scanning to be described later), a tomographic image is reconstructed using the transmitted X-ray data of plural views. The reconstructed scanogram image or tomographic image (axial image, etc.) is displayed on the display device 7 and stored in the storage device 404.

The storage device 404 is formed by a hard disk, etc. and connected to the system control device 401. The transmitted X-ray data collected by the data collection device 206 or reconstructed scanogram image, tomographic image, etc. are stored in the storage device 404. Also, other data such as the program or data for carrying out the function of the X-ray CT apparatus 1 are stored in the storage device 404.

The communications I/F 405 includes devices such as a communication port and a communication control unit for mediating the communication connection among the console 4, the scanner 2 and the table 5 or the communication connection between X-ray CT apparatus 1 and other server devices (not shown in the diagram), and performs transmission/reception of data among the connected respective devices under control of the system control device 8.

Next, the operation of the X-ray CT apparatus 1 will be described referring to the flowchart in FIG. 6 and FIG. 7~FIG. 9.

Figure 6:
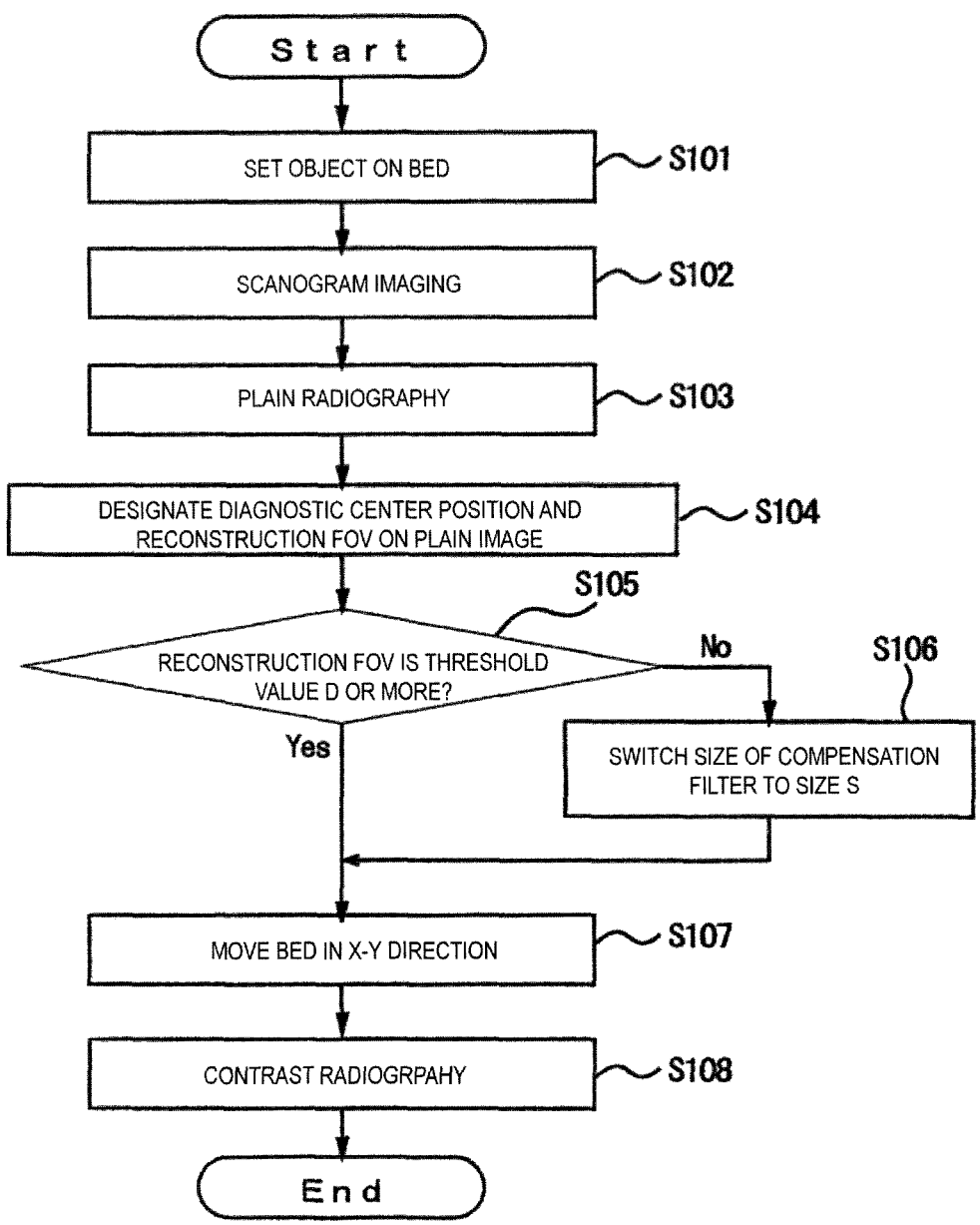
FIG. 6 is a flowchart showing the operation flow of the X-ray CT apparatus 1 related to the present invention (a first embodiment).

The system control device 401 of the X-ray CT apparatus 1 in the present embodiment executes the scanning process shown in FIG. 6. That is, the system control device 401 reads out the program and data in relation to the scanning process from the storage device 404, and executes scanning process based on the read out program and data.

As shown in FIG. 6, the operator first sets the object 6 on the table 5 (step 101). The top plate 51 is inserted into the scanner 2 in the condition that the object 6 is placed on the top plate 51 of the table 5. At this time, the operator executes positioning so that the position of the object 6 in the body-axis direction (z-direction) reaches the scanogram start position and the center position in the side-to-side direction (x-direction) and the body-thickness direction (y-direction) coincides with the scanning center position. The position of the table 5 at this step (real space coordinates) is stored in a RAM as scanning start point $(x_0, y_0, z_0)$.

Next, the system control device 401 obtains a scanogram image in a predetermined range of the object 6 (step S102). The system control device 401 outputs the transmitted X-ray data acquired in the X-ray detector 205 of the scanner 2 to the image processing device 402. The image processing device 402 reconstructs a scanogram image based on the transmitted X-ray data, displays the image on the display device 7 and stores it in the storage device 404.

In the case that an X-ray is irradiated from the lateral direction of the object 6 and the top plate 51 is moved in the body-axis (z) direction, a scanogram image 61 in the LAT direction shown in FIG. 7(A) is obtained. In the case that an X-ray is irradiated from the front side or back side of the object 6 and the top plate 51 is moved in the body-axis (z) direction, scanogram image 62 in the PA direction shown in FIG. 7(B) is obtained.

Figure 7:
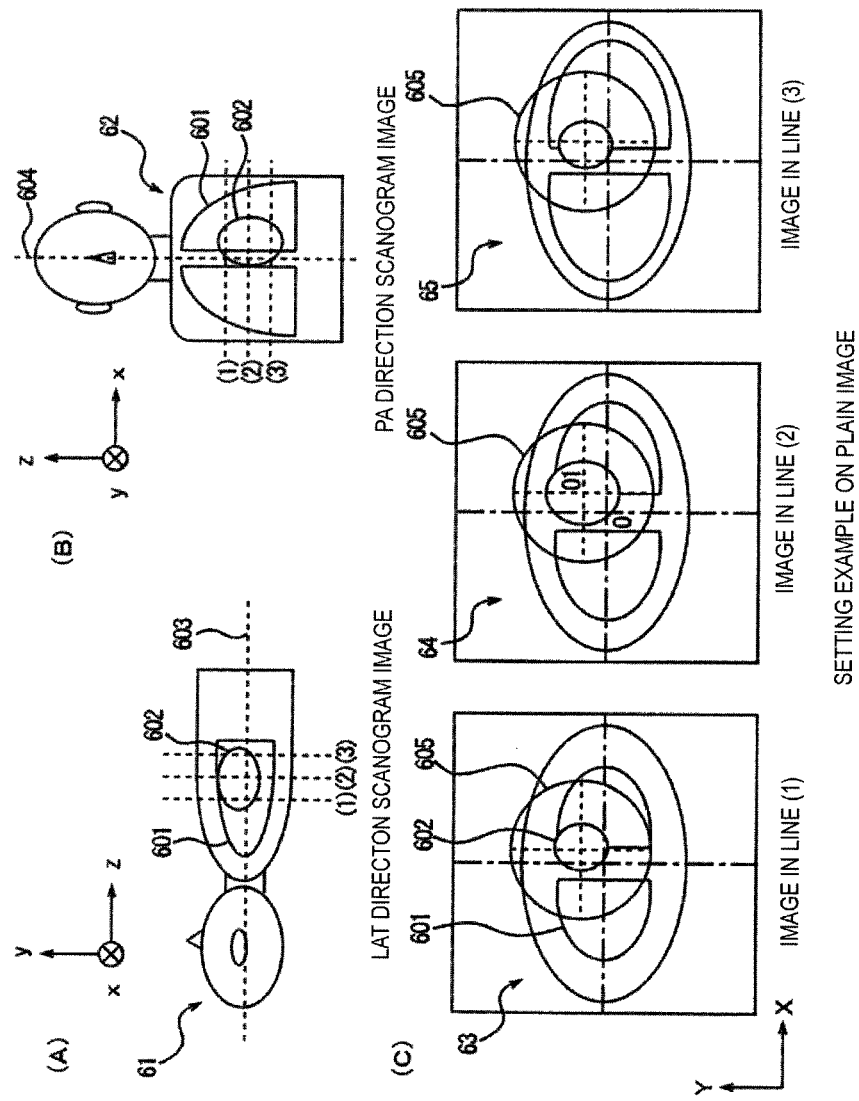
FIG. 7 are examples of designating a diagnostic center position and FOV using: (A) a scanogram image in the LAT direction, (B) a scanogram image in the PA direction and (C) a tomographic image.

In FIG. 7, 601 indicates a lung region, 602 indicates a heart region, 603 and 604 indicate the body axis of object 6. While a scanogram image such as a lung region 601 and a heart region 602 cannot be displayed clearly due to the rib bones surrounding the heart and lungs, FIG. 7 is displayed by omitting the bones for purpose of illustration.

In the case of executing coronary angiography, plain scanning is executed prior to the angiography (step S103). In the plain scanning, a tomographic image is obtained without using contrast agent. The tomographic image obtained by the plain scanning in this step is to be used for designation of a diagnostic center position and a reconstruction FOV.

In the plain scanning, the operator sets various scanning conditions (a scanning range in the z-direction, a reconstruction FOV and other scan conditions) for the plain scanning while referring to scanogram images 61 and 62 shown in FIGS. 7(A) and (B).

The system control device 401 executes a plain scanning based on the set scanning range, reconstruction FOV and scan condition, etc. and acquires the transmitted X-ray data. The compensation filter for using upon the plain scanning is the L-sized compensation filter 301.

The system control device 401 outputs the acquired transmitted X-ray data to the image processing device 402. The image processing device 402 reconstructs each of the tomographic images 63, 64 and 65 as shown in FIG. 7(C) with respect to, for example each of the z-position indicated in (1), (2) and (3) of FIG. 7(A) or (B) based on the transmitted X-ray data, displays the respective images on the display device 7 and stores them in the storage device 404.

Next, the system control device 401 designates diagnostic center position 01 for performing the next angiography and reconstruction FOV, and sets other scan conditions using the tomographic image obtained by the plain scanning (step S104).

In step S104, a circular ROI 605 as shown in FIG. 7(C) may be used as GUI (Graphical User Interface) for designating diagnostic center position 01 and a reconstruction FOV. It is preferable that the center of the circular ROI 605 is clearly indicated using a guide line (dotted line) showing the X-direction and Y-direction on a display screen. The center of the circular ROI 605 is to indicate the diagnostic center position, and the circle corresponds to the reconstruction FOV.

Also, the circular ROI 605 is to be operated by the operation device 8 such as a mouse, for example while the moving operation of the mouse works in conjunction with the movement of the diagnostic center position (the center of circular ROI 605), the operation of the mouse wheel works in conjunction with the radius size of the circular ROI 605, and the click operation of the mouse determines the designation of the diagnostic center position and the FOV. Also in the case, for example that three tomographic images 63, 64 and 65 having different z-positions are displayed on a display screen as shown in FIG. 7(C), it may be set so that when diagnostic center position 01 is designated by the operator moving the circular ROI 605 displayed being superimposed over tomographic image 64 in z-position (2), the circular ROIs 605 with the corresponding radiuses are respectively displayed at the corresponding positions on other tomographic the images 63 and 65, whereby making it possible to confirm the diagnostic center position and the reconstruction FOV in other z-positions (1) and (3).

When the diagnostic center position and the reconstruction FOV are designated, system control device 401 selects the compensation filter in accordance with the size of the designated reconstruction FOV.

In selection of the compensation filter, for example the system control device 401 determines whether or not the size of reconstruction FOV (the radius of circular ROI) which is designated in step S104 is the same or more than a predetermined threshold value D (step S105). When the size of reconstruction FOV is the same or more than threshold value D (step S105; YES), the current L-sized compensation filter 301 is selected. On the other hand, when the size of reconstruction FOV is smaller than threshold value D (step S105; NO), the compensation filter 302 is selected and the command to switch the filter is outputted to the compensation filter switch control device 204 of scanner 2. The compensation filter switch control device 204 switches the filter to the S-sized compensation filter 302 in accordance with the switch command (step S106).

Also, the system control device 401 calculates x-direction distance and y-direction distance of the top plate 51 of the table 5 in the real space based on the distance between diagnostic start point 0 ($X_0$, $Y_0$) and the designated diagnostic center position 01 ($X_1$, $Y_1$), and outputs them to the table control device 501. The table control device 501 moves the top plate 51 according to the calculated distances (step S107). Also, the table control device 501 moves the top plate 51 in the z-direction to the scanning start position of the contrast radiography.

The system control device 401 then receives the setting of the scanning conditions of the contrast radiography, and executes the contrast radiography based on the set scanning conditions (step S108).

While the table 5 is positioned so that the center of body axis coincides with the scanning center position as shown in FIG. 5(A) in the initial setting step of step S101 in FIG. 6, when the designation of the diagnostic center position in step S104 of FIG. 6 and the transfer of the table 5 in step S107 are executed, the top plate 5 is transferred in the x-direction (or the y-direction) as shown in FIG. 5(B) and a heart region at the diagnostic center position reaches the scanning center position.

Also in step S105, when the radius of reconstruction FOV is determined as being smaller than the predetermined threshold value D, the S-sized compensation filter 302 is to be used.

Figure 8:
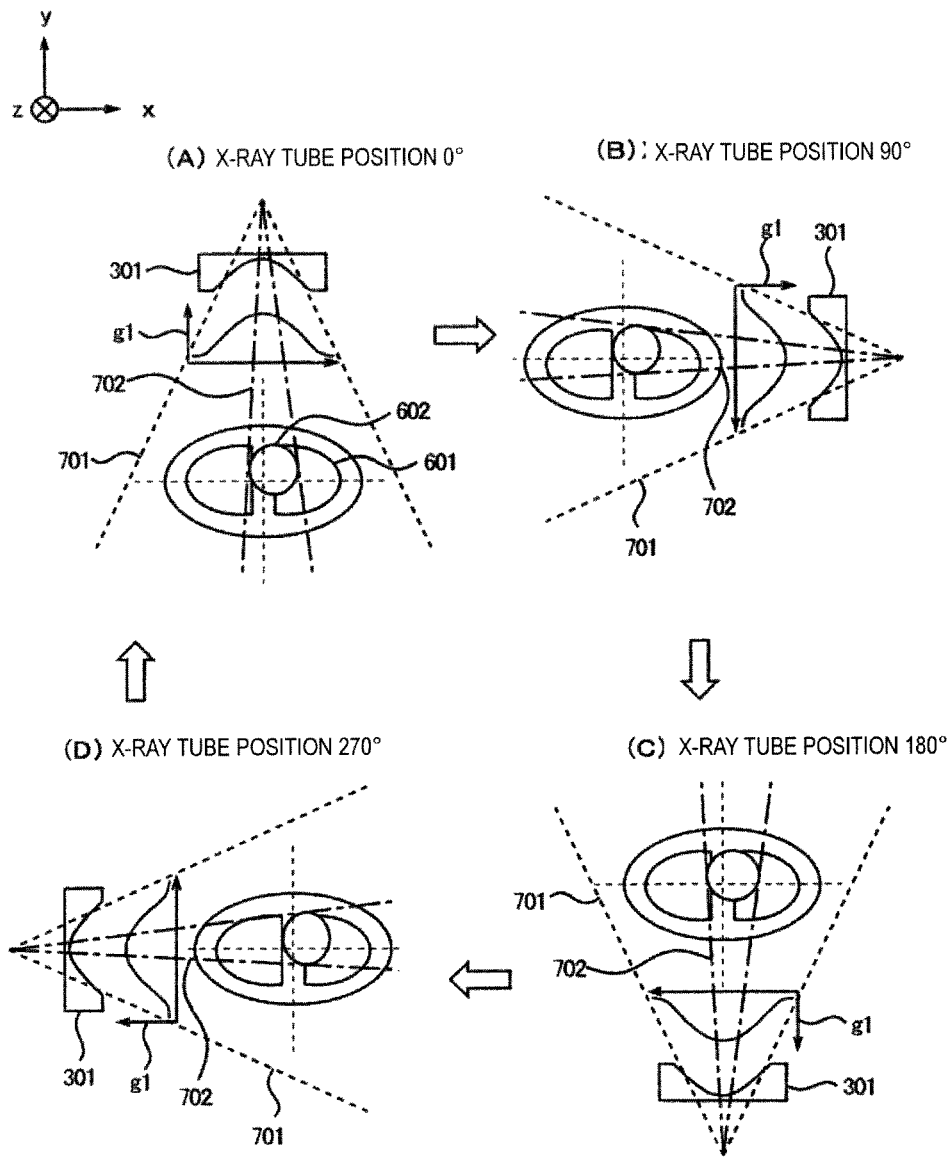
FIG. 8 is for explaining the X-ray irradiation width in accordance with a scan angle in the case of scanning a heart region while the heart is at an offset position (the conventional scan).

As shown in FIG. 8, in the conventional scanning, contrast radiography of a heart is executed by positioning object 6 at the same position as the time of initial setting (the center of the x-position and y-position of the object 6 are coincided with the scanning center position) using the L-sized compensation filter 301.

In FIG. 8, a dotted line 701 indicates the open angle of the irradiated X-ray, and a chained line 702 indicates the open angle of the X-ray exposed to the heart.

In the conventional method, in each of the scan angles, the scanning has been executed using the region having the highest X-ray intensity to a somewhat low intensity, since the heart is not positioned at the center of scanning. Also, since the curvature in the curve of the compensation filter is small, attenuation of X-ray intensity in the surrounding area is also small, thus the X-ray having a comparatively high intensity is exposed to the surrounding area of the heart.

Figure 9:
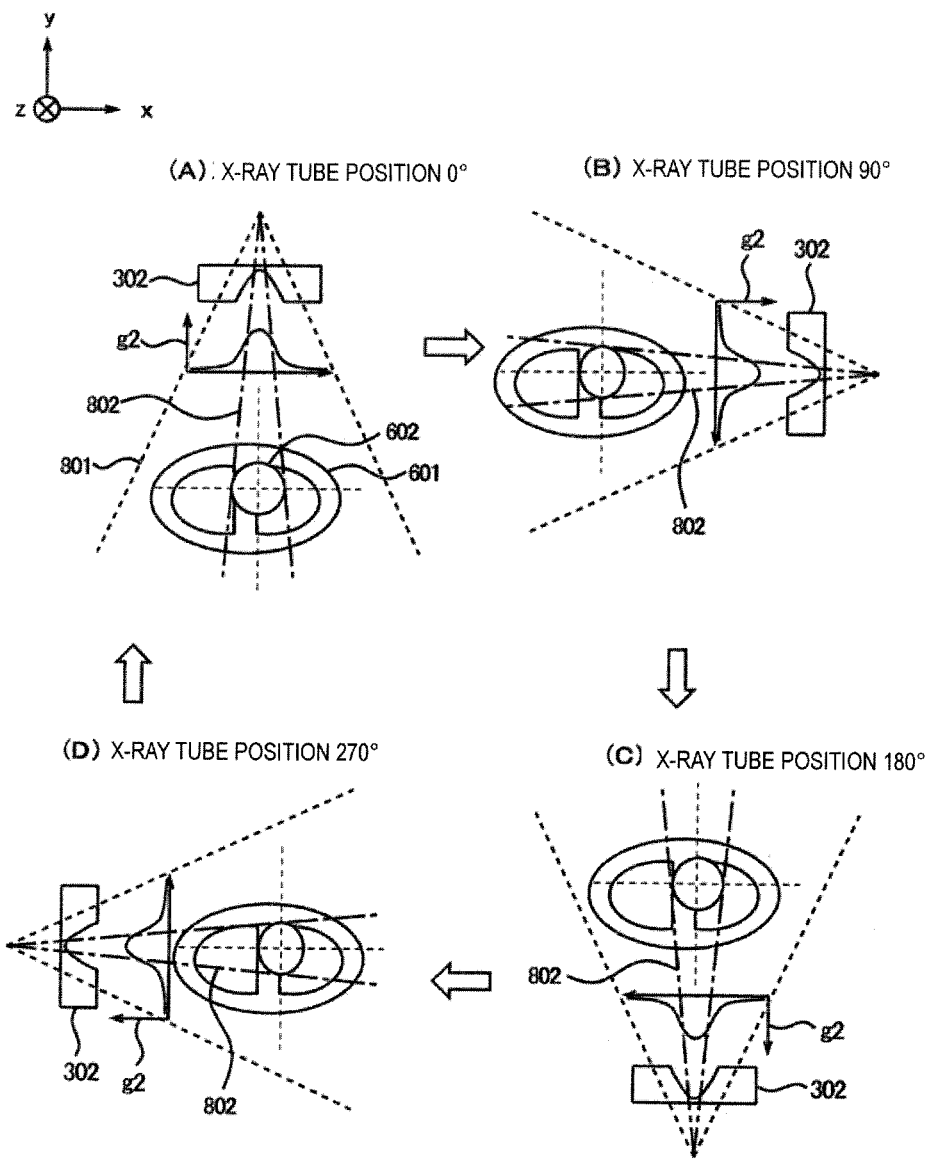
FIG. 9 is for explaining the X-ray irradiation width in accordance with a scan angle in the case of setting a heart region at the diagnostic center position (the scan in the present invention).

On the other hand, in the case that the radiography is executed by setting the heart region as the scanning center position and the reconstruction FOV is focused to the heart region as in the scanning process of the present embodiment, top plate 5 is moved so that the heart region reaches the scanning center position, and the compensation filter is switched to S-sized compensation filter 302 according to the reconstruction FOV as shown in FIG. 9. In FIG. 9, a dotted line 801 indicates the open angle of the irradiated X-ray, and a chained line 802 indicates the open angle of the X-ray exposed to the heart.

In comparison with FIG. 8 (conventional method), the region having the highest X-ray intensity is used for the X-ray to be exposed to the center of the heart and the X-ray intensity to be exposed to the surrounding area of the heart has the smaller intensity compared to the L-sized compensation filter 301 in each scan angle of FIG. 9 (present embodiment). As a result, the effect of exposure attenuation in the surrounding area of the heart can be attained. Also, since the target organ (heart) is at the center of scan, the spatial resolution is improved which enables acquisition of a contrast-enhanced image with high quality.

As described above, the X-ray CT apparatus of the present embodiment comprises a plurality of compensation filters for adjusting the irradiation distribution of X-rays. When an operator designates a diagnostic center position and a reconstruction FOV using a tomographic image by clicking a mouse, the system control device 401 moves the top plate 51 of the table 5 in the up-and-down and side-to-side directions (x-direction, y-direction and z-direction) so that the designated diagnostic center position reaches the scanning center position. Also, the system control device 401 selects a suitable compensation filter according to the designated reconstruction FOV and switches to the selected filter. As for the compensation filters, at least the compensation filter having a large X-ray irradiation distribution width (size L) in the scanner-turning direction and the compensation filter having a small X-ray irradiation distribution width (size S), and when the size of the designated reconstruction FOV (for example, the radius of reconstruction FOV) is smaller than a predetermined threshold value, the filter is switched to the S-sized compensation filter 302.

Therefore since a target organ (heart) can be scanned while being moved to the scanning center, the scanning can be executed by using the region having the largest X-ray intensity in all of the scan angles. Accordingly, the spatial resolution is improved resulting in the attainment of high image quality. Also, by switching the compensation filter 301 to size S, exposure of X-rays can be focused to a target organ (heart), thereby radiation exposure to the surrounding area of the target organ can be attenuated.

Also, by clicking the center of target region (heart) on a plain CT image (tomographic image) prior to the contrast radiography, a table can be moved in the up-and-down and side-to-side directions and the target region can be set at the optimum position.

In this manner, the influence due to the overlap of organs or bones can be reduced compared to the method of designating the diagnostic center position using a scanogram image, thereby making it possible to designate the diagnostic center position more accurately.

Second Embodiment

Next, a second embodiment of the X-ray CT 1 apparatus related to the present invention will be described.

Since the X-ray CT apparatus in the second embodiment has the same hardware configuration as the X-ray CT apparatus 1 as in the above-described first embodiment, the same function parts are represented by the same reference numerals and the detailed description on the configuration is omitted.

Figure 10:
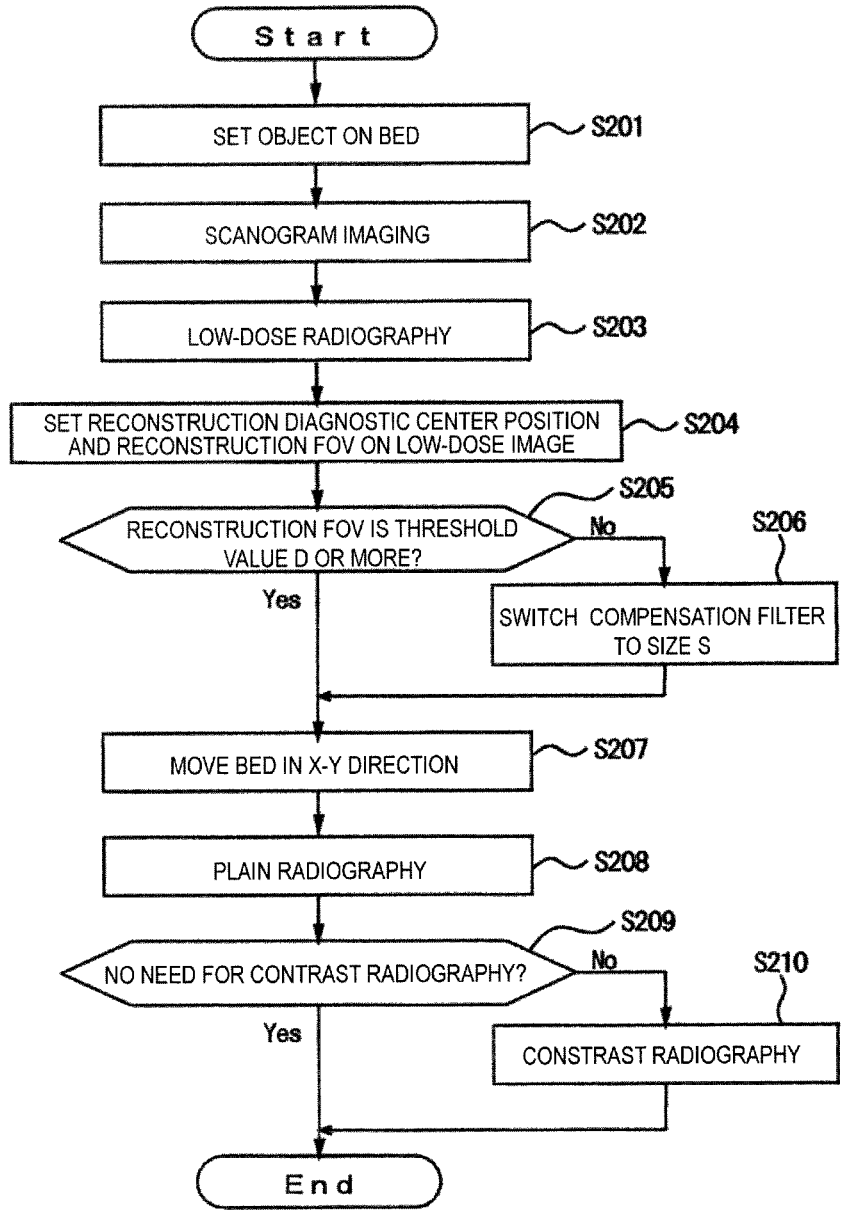
FIG. 10 is a flowchart showing the operation of X-ray CT apparatus 1 related to the present invention (a second embodiment).

As shown in FIG. 10, the X-ray CT apparatus 1 in the second embodiment executes a low-dose radiography (refer to step S203 in FIG. 10) prior to a plain scanning or contrast radiography.

In a low-dose radiography, the X-ray dose for irradiating to an object can be less than the dose to be used in the general radiography. While the X-ray dose for irradiation to an object is generally varied depending on a scan target region or the objective of scanning, the low-dose radiography in the present embodiment means that a tomography is scanned having the image quality capable enough to designate a diagnostic center position and a reconstruction FOV. For example, a tomographic image is to be scanned with the tube current amount which is less than 20%, more preferably less than 10% of that used in normal scanning. Or, the tube voltage may be reduced. The helical pitch of the low-dose radiography may be set as a high pitch such as the normal condition for scanning an abdominal region.

The operation flow of the X-ray CT apparatus 1 in the second embodiment will be described.

As shown in FIG. 10, an operator first sets an object on a table as in steps S101~S102 of the first embodiment (step S201) and obtains a scanogram image (step S202). Next, using the obtained scanogram image, the operator sets z-range, scanning conditions, etc. for the low-dose radiography and starts scanning with the above-described low dose of X-ray (step S203). The compensation filter to be used at this time is the L-sized compensation filter 301.

The system control device 401 reconstructs a tomographic image obtained by low-dose radiography in the image processing device 402, displays the reconstructed image on the display device 7, and receives the diagnostic center position and the reconstruction FOV (step S204). The processing in step S204 is the same as step S104 in the first embodiment.

Then in the same manner as step S105~step S107 of the first embodiment, after switching the compensation filter according to the reconstruction FOV (step S205~step S206) and moving table 5 in accordance with the diagnostic center position (step S207), a plain scanning is executed (step S208). In the plain scanning, the imaging conditions capable of acquiring a desired image quality are to be set. Also after executing the plain scanning, the contrast radiography is to be executed as need arises (steps S209~S210).

As described above, the X-ray CT apparatus 1 of the second embodiment receives the designation of the diagnostic center position or the reconstruction FOV prior to a plain scanning, sets the designated diagnostic center position (for example, a heart) as the scanning center position, and executes the plain scanning with the enough X-ray dose to satisfy a desired image quality in the condition that the compensation filter is switched to a suitable one.

Since both a plain scanning and a contrast radiography are not necessarily executed in a normal examination, it is preferable to execute the examination by the method of second embodiment when only an image by the plain scanning is necessary. As a result, it is possible to improve the image quality of the tomographic image obtained by the plain scanning and reduce radiation exposure to the other regions besides the target region more than the first embodiment. The present embodiment can reduce irradiation exposure to the surrounding area of a target region even in the case that contrast radiography is to be executed after the execution of plain scanning.

The preferable embodiments of the X-ray CT apparatus according to the present invention have been described. However, the present invention is not limited to these embodiments. For example, while the X-ray CT apparatus of the gantry type is exemplified in the above embodiments, the C-arm type of X-ray CT apparatus may also be used. Also, while the case of designating a heart region as the center of diagnosis is exemplified in the above-described X-ray CT apparatus, the designation method can be applied also to regions such as a shoulder, a single lung, an upper limb or a lower limb.

Also, while compensation filters are exemplified as two kinds of size L and size S in the above-described embodiments, a plurality of compensation filters of other sizes or the filters having different X-ray irradiation distributions may be comprised. In this case, in selection of the compensation filter in step S105 of FIG. 6 or in step S205 of FIG. 10, a plurality of threshold values in accordance with the number of compensation filters may be used or the table in which the compensation filters to be selected are set according to a scan region may be prepared in the system control device 401.

Also while the circular ROI 605 is used in the above-described designation operation of a diagnostic center position or a reconstruction FOV, an operator may input the desired coordinates or values or use other GUI in place of using the ROI 605. It is also obvious that persons skilled in the art can make various kinds of alterations or modifications within the scope of the technical idea disclosed in this application, and it is understandable that they belong to the technical scope of the present invention.

DESCRIPTION OF REFERENCE NUMERALS

1: X-ray CT apparatus, 2: scanner, 4: console, 5: table, 51: top plate, 6: object, 7: display device, 8: operation device, 201: X-ray tube (X-ray source), 203: collimator case, 204: compensation filters switch control device, 205: X-ray detector, 401: system control device, 402: image processing device, 501: table control device, 502: x-direction movement mechanism, 503: y-direction movement mechanism, 504: z-direction movement mechanism, 605: circular ROI, 0: diagnostic start point, 01: diagnostic center position, x, y, z: real space coordinates, X, Y: coordinates on display screen

The invention claimed is:

1. An X-ray CT apparatus comprising:
   a scanner in which an X-ray source for irradiating an X-ray to an object to be examined and an X-ray detector for detecting the X-ray which transmitted through the object are placed opposite from each other, configured to revolve around the object; and
   a table having a top plate movable in the body-axis direction of the object, the side-to-side direction or the up-and-down direction while being perpendicular to the body-axis direction,
   configured to reconstruct a tomographic image of an object based on the transmitted X-ray data detected by the X-ray detector and display the reconstructed image on display means,
   wherein the scanner is provided with a compensation filter configured to adjust irradiation distribution of the X-ray irradiated from the X-ray source,
   characterized in further comprising:
   designation means configured to receive a designation of a diagnostic center position and a reconstruction FOV of the object using the tomographic image;
   top plate moving means configured to move a top plate of the table in the body-axis direction, the side-to-side direction or the up-and-down direction so that the diagnostic center position designated by the designation means reaches a scanning center position; and
   scanning means configured to execute a tomography using contrast agent or with desired image quality in the condition that a top plate is moved by the top plate moving means.

2. The X-ray CT apparatus according to claim 1, characterized in that plural numbers of the compensation filters are provided, further comprising compensation filter switching means configured to select a suitable compensation filter according to the reconstruction FOV designated by the designation means and switch to the selected suitable compensation filter, wherein the scanning means executes tomography in the condition that the switching of compensation filters is carried out by the compensation filter switching means.

3. The X-ray CT apparatus according to claim 1, characterized in that the tomographic image of the object is scanned while the X-ray dose is reduced to the amount enough to acquire the image quality capable of designating a diagnostic center position and a reconstruction FOV.

4. The X-ray CT apparatus according to claim 2,
characterized in that the compensation filter at least includes a first filter and a second filter having different shapes in which the second filter distributes an X-ray to a narrower range in the scanner-turning direction compared to the first filter,
wherein the compensation filter switching means, in the case that the size of reconstruction FOV designated by the designation means is the same or smaller than a predetermined threshold value, selects the second filter and switches to the selected filter.

5. A tomography method by an X-ray CT apparatus comprising:
a scanner in which an X-ray source for irradiating an X-ray to an object to be examined and an X-ray detector for detecting the X-ray which is transmitted through the object are placed opposite from each other, configured to revolve around the object; and
a table having a top plate movable in the body-axis direction of the object, the side-to-side direction or up-and-down direction while being perpendicular to the body-axis direction,
wherein the scanner is provided with a compensation filter configured to adjust irradiation distribution of the X-ray irradiated from the X-ray source,
configured to reconstruct a tomographic image of the object based on the transmitted X-ray data detected by the X-ray detector and display the reconstructed image on display means,
characterized in further comprising steps of:
receiving a designation of a diagnostic center position and a reconstruction FOV of the object using the tomographic image;
moving a top plate of the table in the body-axis direction, the side-to-side direction or the up-and-down direction so that the diagnostic center position reaches a scanning center position; and
executing a tomography using contrast agent or with desired image quality in the condition that a top plate is moved.

6. The X-ray CT apparatus according to claim 2, characterized in that the tomographic image of the object is scanned while the X-ray dose is reduced to the amount enough to acquire the image quality capable of designating a diagnostic center position and a reconstruction FOV.

* * * * *